_United States Patent_ [19]

Laustsen et al.

[11] Patent Number: 6,080,564

[45] Date of Patent: *Jun. 27, 2000

[54] SELECTIVE INACTIVATION OF ASPERGILLUS PROTEASES

[75] Inventors: Mads Aage Laustsen, Lyngby; Stig Nielsson, Lynge, both of Denmark

[73] Assignee: Novo Nordisk A/S, Bagsvaerd, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 09/076,460

[22] Filed: May 12, 1998

Related U.S. Application Data

[63] Continuation of application No. PCT/DK96/00489, Nov. 25, 1996.

[30] Foreign Application Priority Data

Dec. 7, 1995 [DK] Denmark ................. 1392/95

[51] Int. Cl.⁷ ................. C12N 9/99; C12N 9/00
[52] U.S. Cl. ................. 435/184; 435/183; 435/814
[58] Field of Search ................. 435/184, 183, 435/814

[56] References Cited

U.S. PATENT DOCUMENTS

| | | |
|---|---|---|
| 2,683,682 | 7/1954 | Miller et al. ............. 435/184 |
| 3,446,706 | 5/1969 | Beuk ..................... 435/184 |
| 4,086,139 | 4/1978 | Hoerle ................... 435/184 |
| 4,235,970 | 11/1980 | Leach et al. ............. 435/202 |
| 4,299,848 | 11/1981 | De Stefanis et al. ....... 426/20 |
| 4,518,697 | 5/1985 | Bartnik et al. ........... 435/254 |
| 4,532,213 | 7/1985 | Shetty et al. ............ 435/225 |
| 4,784,860 | 11/1988 | Christensen et al. ....... 426/46 |
| 5,252,726 | 10/1993 | Woldike .................. 536/24.1 |
| 5,420,029 | 5/1995 | Gelfand et al. ........... 435/194 |
| 5,424,203 | 6/1995 | Vicenzi .................. 435/184 |
| 5,594,119 | 1/1997 | Yaver et al. ............. 536/23.2 |
| 5,674,728 | 10/1997 | Buxton et al. ............ 435/225 |

FOREIGN PATENT DOCUMENTS

| | | |
|---|---|---|
| 0 021 179 | 1/1981 | European Pat. Off. . |
| 1281232 | 5/1962 | France . |
| 90/13638 | 11/1990 | WIPO . |
| 97/20921 | 6/1997 | WIPO . |

*Primary Examiner*—Jon P. Weber
*Attorney, Agent, or Firm*—Steven T. Zelson, Esq.; Reza Green, Esq.

[57] ABSTRACT

A method is presented for inactivating undesired acid labile proteases which are expressed into the culture medium simultaneously with desired enzymes by Aspergillus species when Aspergillus species is used as the host for recombinantly producing enzymes. The method involves incubating culture medium which contains a mixture of the desired recombinantly produced enzyme and the undesired acid labile protease which have been expressed therein at pH values below 4.5 and at temperatures from 2° C. to 75° C. for at least 20 seconds.

13 Claims, 6 Drawing Sheets

```
                          SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: substrate

<400> SEQUENCE: 1

Ala Ala Pro Phe
```

SELECTIVE INACTIVATION OF ASPERGILLUS PROTEASES

CROSS-REFERENCE TO RELATED APPLICATIONS

This application is a continuation of PCT/DK96/00489 filed Nov. 25, 1996 and claims priority under 35 U.S.C. 119 of Danish application 1392/95 filed Dec. 7, 1995, the contents of which are fully incorporated herein by reference.

TECHNICAL FIELD

The present invention relates to a method for inactivation of one or more undesirable enzymes in a mixture of enzymes containing a desirable enzyme.

BACKGROUND ART

It is well known in the art that when fermenting a microorganism in order to obtain a desirable enzyme, one or more undesirable enzymes are often also expressed by said microorganism. If these undesirable enzymes are not effectively inactivated they may cause huge stability problems during recovery of the desirable enzyme and/or during storage of the desirable enzyme. Even if these other enzymes do not cause stability problems they may indeed be unwanted as industry for many purposes requires a "pure" enzyme without side-activities.

In order to solve the above mentioned problem many suggestions have been put forward: Hoerle et al. disclose in U.S. Pat. No. 4,086,139 use of hypochlorite and chlorite ions to inactivate amylase in an amylase-protease mixture; Bock et al. describe in DD 216 955 that polygalacturonases may be removed from a pectinase mixture by adding urea, and DeStefanis et al disclose in EP 021 179 that Bacillus proteases may be inactivated in a protease-amylase mixture by adjusting the system to a pH between 5.0 and 7.0, buffering said mixture with a buffering agent, and heating said mixture to a temperature of from 40° C. to 75° C.

It is an object of the present invention to provide a method for inactivation of undesirable enzymes in a mixture of enzymes which method should have short process times, result in high yields, and at the same time be simple, inexpensive and compatible to industrial requirements.

SUMMARY OF THE INVENTION

It has surprisingly been found that many undesirable enzymes may be effectively inactivated by use of the present invention.

Accordingly, the invention relates to a method for inactivation at least one undesirable enzyme in a mixture of enzymes containing a desirable enzyme comprising the steps of
a) holding the mixture at a temperature of from 2° C. to 75° C. at a pH below 5.0 for a period of at least 20 sec.; and/or
b) holding the mixture at a temperature of from 2° C. to 75° C. at a pH above 9.0 for a period of at least 20 sec.

BRIEF DESCRIPTION OF DRAWINGS

The present invention is further illustrated by reference to the accompanying drawings, in which.

DETAILED DISCLOSURE OF THE INVENTION

Figure 1:
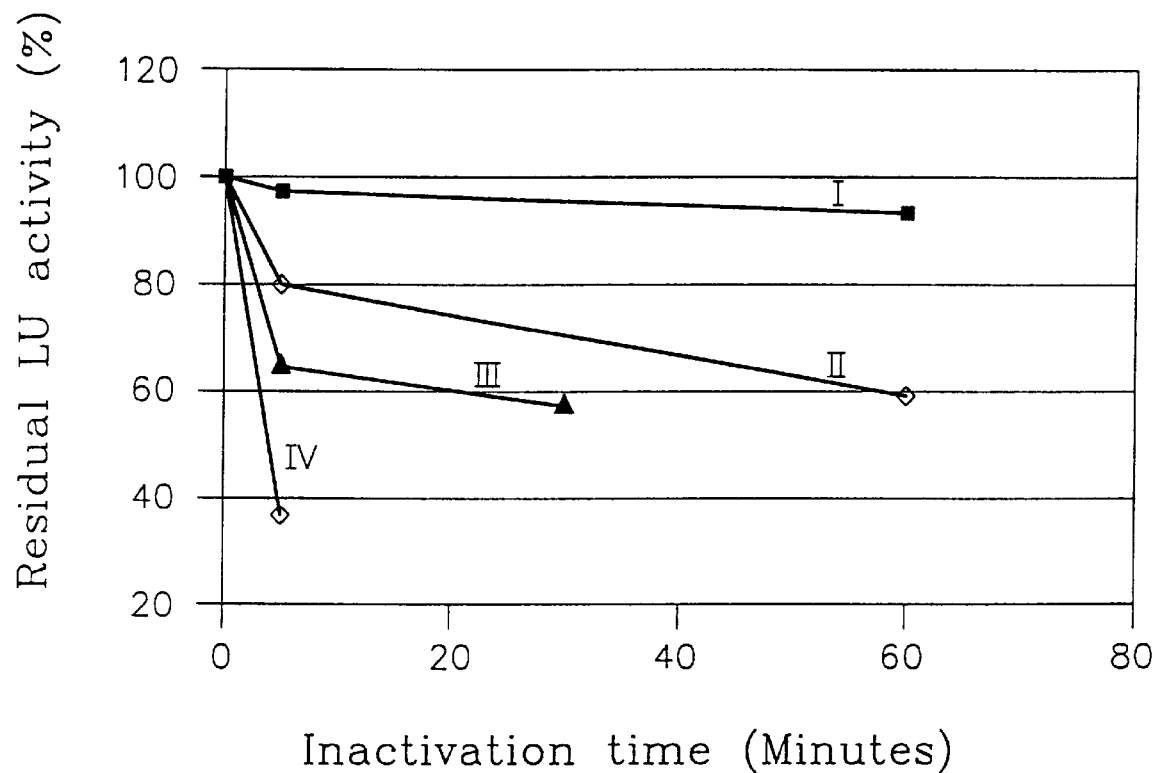
FIG. 1 shows the lipase activity versus inactivation time at pH 3.5 and at 45° C. (I), at 50° C. (II), at 55° C. (III) and at 70° C. (IV), the experiments performed as described in Example 1.

The present invention relates to a method for inactivation at least one undesirable enzyme in a mixture of enzymes containing a desirable enzyme comprising the steps of
a) holding the mixture at a temperature of from 2° C. to 75° C. at a pH below 5.0 for a period of at least 20 sec.; and/or
b) holding the mixture at a temperature of from 2° C. to 75° C. at a pH above 9.0 for a period of at least 20 sec.

The principle we use in the present invention is that an enzyme normally either is able to tolerate acidic (pH below 5.0) or alkaline conditions (pH above 9.0). We combine this fact with the temperature tolerance of the enzyme in question (2° C. to 75° C.) and the time we hold the enzyme mixture at said conditions in order to get the optimum conditions where most of the desirable enzyme is maintained and most of the undesirable enzyme is inactivated. So the method operates in a system where three parameters can be varied: the pH, the temperature and the holding time.

It may in some cases be an advantage to add a stabilizer, which stabilize the desirable enzyme; this stabilizer should be added before the method of the invention is used. Examples of such stabilizers are inhibitors, co-factors or substrates for the desirable enzyme: It is well known in the art that when an enzyme is bound to an inhibitor, to a co-factor or to a substrate (e.g. carboxymethylcellulose (CMC)) it becomes more stable. An example, wherein CMC is used, is given in Example 7.

It may also in some cases be an advantage to add a destabilizer, which destabilize the undesirable enzyme; this destabilizer should be added before the method of the invention is used. Useful destabilizers may be complexing agents, in particular metal ion complexing agents such as EDTA and EGTA.

Furthermore, it may in some cases be an advantage both to add a stabilizer, which stabilize the desirable enzyme, and a destabilizer, which destabilize the undesirable enzyme.

Undesirable Enzymes

A very common undesirable class of enzymes is the proteolytic enzymes (proteases, peptidases) as they are able to degrade proteins, and as enzymes are proteins, proteolytic enzymes are able to degrade the desired enzyme.

However, really all enzymes obtained from e.g. animals, plants or microorganisms, may be undesirable as the industry is asking for more and more "pure" enzymes, or "monocomponent" enzymes, i.e., any enzyme activity but the desired, is unwanted.

So undesirable enzymes may be any enzyme, in particular an enzyme selected from the group consisting of lipases, amylases, cellulases, oxidoreductases, xylanases, isomerases, peptidases and proteases.

Desirable Enzymes

Any enzyme obtainable from, e.g., a microorganism, an animal or a plant may be desirable. In particular an enzyme selected from the group consisting of lipases, amylases, cellulases, oxidoreductases, xylanases, isomerases, peptidases and proteases is preferred.

The method of the invention is especially useful when the desirable enzyme is obtainable from a microorganism, an animal or a plant, in particular from a fungus, preferably a filamentous fungus such as Aspergillus, e.g., *A. oryzae, A. niger*, or Humicola, e.g., *H. insolens*.

Especially when the desirable enzyme is cloned into a filamentous fungus such as Aspergillus or Humicola, there is today a problem in getting rid of undesirable enzymes, typically traces of protease activity. The amount of the undesirable enzymes present is typically very low, often not detectable with standard methods, but as the cloned enzyme is not used to these enzymes—even very small amounts of these undesirable enzymes make the cloned (=the desirable) enzyme unstable. By using the method of the invention it is possible to inactivate these very small amounts of proteolytic activity, whereby a product with a very good stability may be obtained (for reference see Example 1).

Mixture of Enzymes

The method of the invention may be used on any mixture of enzymes which contains at least two enzymes. The method is particularly useful when the mixture of enzymes is a culture (=fermentation) broth.

The method of the invention may be applied to an untreated culture broth (whole culture broth), to a homogenized culture broth, or to a whole or homogenized culture broth that has been subjected to, e.g., a water dilution and/or one or more solid/liquid separatory techniques such as flocculation, centrifugation, filtration, e.g., drumfiltration or filter press filtration, or membrane separation, optionally followed by a membrane concentration or evaporation.

According to the invention the membrane concentration may be performed using any membrane equipment known in the art, but it is preferred that the membrane concentration is done using ultrafiltration techniques such as hollow fiber, spiral rounds or plate and frame units. The preferred cut off value will depend on the properties of the enzyme in question but usually a cut off value in the interval of from 1 to 100 kD is preferred.

The enzyme solution may further be purified in a variety of ways such as by using filtration, chromatographic methods, adsorption and/or precipitation/crystallization processes before the undesirable enzyme activities are inactivated according to the invention.

If the desirable enzyme is very unstable it may be advisable to inactivate the undesirable enzyme(s) as soon as possible after fermentation, typically after a filtration, e.g., after a centrifugation or a drumfiltration.

If the desirable enzyme is less unstable it may be an advantage to wait with the inactivation until the fermentation broth has been purified and concentrated; typically after a filtration and an ultrafiltration has taken place.

After the inactivation according to the invention has taken place the enzyme product is processed in the usual way; i.e. it may be further purified in a variety of ways such as by using filtration, concentration, chromatographic methods, adsorption and/or precipitation/crystallization processes.

In some cases the undesirable enzyme(s) are just inactivated, in other cases it may be an advantage to inactivate and remove the undesirable enzyme(s). The removal of the undesirable enzyme(s) is typically done by a solid/liquid operation.

Use of the Method

When having a mixture of enzymes containing a desirable enzyme and one or more undesirable enzymes, it is advisable first to look at the pH-curve for the desirable enzyme and see whether it has optimum to the alkaline or the acidic side. If the desirable enzyme has optimum to the acidic side, it means that it is normally not destroyed at a pH below 5.0. It is then recommended to run a test series combining various pH-values (e.g. pH 4.5, pH 4.0, pH 3.5) with various temperatures-values (e.g. 40° C., 50° C., 60° C., 70° C.) and various holding times (e.g. 1 minute, 5 minutes, 60 minutes, 240 minutes). By doing this optimum conditions can be found where most of the desirable enzyme is stored and most of the undesirable enzyme(s) are inactivated.

It is preferred to hold the pH as acidic or as alkaline as possible, so according to the present invention, a method, wherein said enzyme mixture is adjusted to a pH below 4.5, in particular to a pH below 4.0, especially to a pH below 3.5, or wherein said enzyme mixture is adjusted to a pH above 9.5, in particular to a pH above 10.0, is preferred.

According to the invention the temperature should be held in the range of from 2–75° C., in particular in the range of from 10–70° C., preferably in the range of from 25–65° C., even more preferably in the range of from 40–60° C.

According to the invention the pH may be adjusted first whereafter the solution is heated/cooled to the desired temperature (as illustrated in Example 1), or the solution may be heated/cooled to the desired temperature first, whereafter the pH is adjusted (as illustrated in Example 3).

The holding time may be anything from 20 sec. to a couple of weeks, typically the holding time will be in the range of from 1 minute to 24 hours, preferably in the range of from 1 minute to 4 hours.

Depending on the desirable and the undesirable enzyme(s) in question it is difficult to say how much of the undesirable enzyme(s) should be inactivated and how much of the desirable enzyme should be maintained. Normally a reduction of the undesirable enzyme(s) to a level of less than 15% of the initial level after the inactivation according to the invention is preferred, in particular to a level of less than 10% of the initial level after the inactivation according to the invention is preferred, even more preferably to a level of less than 2% of the initial level after the inactivation according to the invention is preferred, especially to a level of less than 1% of the initial level after the inactivation according to the invention is preferred.

Normally it can only be accepted that at maximum half of the desirable enzyme is inactivated, so accordingly, it is preferred that the level of the desirable enzyme is more than 50% of the initial level after the inactivation according to the invention, in particular more than 60% of the initial level after the inactivation according to the invention, preferably more than 75% of the initial level after the inactivation according to the invention, even more preferably more than 85% of the initial level after the inactivation according to the invention.

Adjusting pH

For adjustment of pH virtually any acid or base can be used. The acid may be inorganic or organic. Some examples are hydrochloric acid, sulfuric acid, nitrous acid, phosphoric acid, acetic acid, citric acid, and formic acid. Preferred acids are formic acid, citric acid, and acetic acid. Preferred bases are sodium hydroxide, potassium hydroxide, and ammonium hydroxide, in particular sodium hydroxide.

The following examples further illustrate the present invention; they are not intended to be in any way limiting to the scope of the invention as claimed.

In the examples the enzyme activities were determined using one of the following assays:

Determination of Lipase Activity

Lipase activity in Example 1, 2, 3, 4 and 5 was assayed using glycerine tributyrat as a substrate and gum-arabic as an emulsifier. 1 LU (Lipase Unit) is the amount of enzyme which liberates 1 μmole titratable butyric acid per minute at 30° C., pH 7.0. The lipase activity was assayed by pH-stat using Radiometer titrator VIT90, Radiometer, Copenhagen.

Determination of Protease Activity

Protease activity in Example 1, 2, 3 and 8 was assayed using ala-ala-pro-phe-p-nitro anilide SEQ ID NO:1 as a substrate. When hydrolyzed, the p-nitro anilide (pNA) group is liberated, causing a yellow colour that can be measured spectrophotometrically at 405 nm.

The reaction conditions were 30° C., pH 9.5 using a 0.05 M borate/KCl buffer, and the substrate concentration was 2.5 mM pNA-peptide.

The change over time in absorbance at 405 nm was measured with an automatic system, <Cobas>FARA, and one unit of activity (1 U) was defined as the amount of enzyme capable of hydrolyzing 1 μmole pNA-peptide per minute.

Determination of Cellulase Activity (Endo Glucanase Activity) Using Viscosimeter and CMC Cellulase activity in Example 7 was assayed using Carboxy Methyl Cellulose, CMC (Hercules 7 LFD) as a substrate. When hydrolyzed the viscosity of the incubation mixture is lowered and measured using a vibration viscosimeter. The incubation is done at pH=9.0 in 0.1 M tris at 40° C. for 30 minutes. The viscosity is measured using a vibrating rod-viscosimeter type MIVI 3000 (Sofrase).

Determination of Cellulase Activity (Endo Glucanase Activity) Using IEF with CMC Cellulase activities in Example 6 were assayed using Iso Electrical focusing with a CMC topagar overlay. A Pharmacia Ampholine PAGplate, pH 3.5–9.5 for IEF was used (Code no. 80-1124-80).

The top agar was prepared using 0.5% CMC (Hercules 7 LFD)+1% agarose (Litex LSA) in tris maleic acid buffer (pH=7). The suspension is heated to the boiling point for 5 minutes whereafter it is cooled to 55° C.

After focusing the pH gradient is removed by succeeding flush using tris maleic acid buffer (pH=7) for one hour. Subsequently the top agar is casted on the top of the gel. The identification has been done after 6 hours at 45° C. A solution of 0.1% Congo red in tris maleic acid buffer (pH=7) is poured over the topagar after which it is left for 10 minutes and decolorized with 1 M NaCl in H2O for 2×10 minutes.

Endoglucanase activity is seen as clearing zones on a red background. The quantification has been done on a BioImage gel scanning system. The zones scanned represent the amount of cellulase activities.

Determination of Protease Activity Using IEF with Casein

Protease activity in Example 7 was assayed using Iso Electrical focusing with a Casein topagar overlay. A Pharmacia Ampholine PAGplate, pH 3.5–9.5 for IEF was used (Code no. 80-1124-80).

The top agar was prepared using a mixture of 1% Casein+ 1% agarose (Litex LSA) in tris maleic acid buffer (pH=7). The agarose is heated to the boiling point for 5 minutes after which it is cooled to 55° C. After focusing the pH gradient is removed by succeeding flush using tris maleic acid buffer (pH=7) for one hour. Subsequently the top agar is casted on to the gel after mixing 1 vol of 1% casein and 1 vol of 1% agarose.

Protease activity is seen as precipitated zones of hydrolysed casein. The quantification is done on a BioImage gel scanner. The scanned zones represent the amount of protease activities.

EXAMPLE 1

Inactivation of Protease

This example describes the inactivation of undesired proteases in a concentrate at low pH leaving a desired lipase.

A culture broth containing lipase B, obtained as described in WO 88/02775 by cloning *Candida antarctica* lipase B into an *Aspergillus oryzae* host, in which culture broth an undesired protease is inactivated according to the method of invention.

Initially, the culture broth was subjected to solid/liquid separation by drum filtration. Subsequently the drumfiltrate was subjected to UF-concentration on membranes with a cut off of 20 kD. The concentrate was adjusted to pH=3.5 using 10% phosphoric acid and then heated to various temperatures within the interval of from 45° to 70° C., (at 45° C. (I), at 50° C. (II), at 55° C. (III) and at 70° C. (IV)).

After various minutes within the interval of 0–60 minutes samples were adjusted to pH=8.0 using 13% sodium hydroxide, cooled and analyzed for lipase and protease activity.

Figure 2:
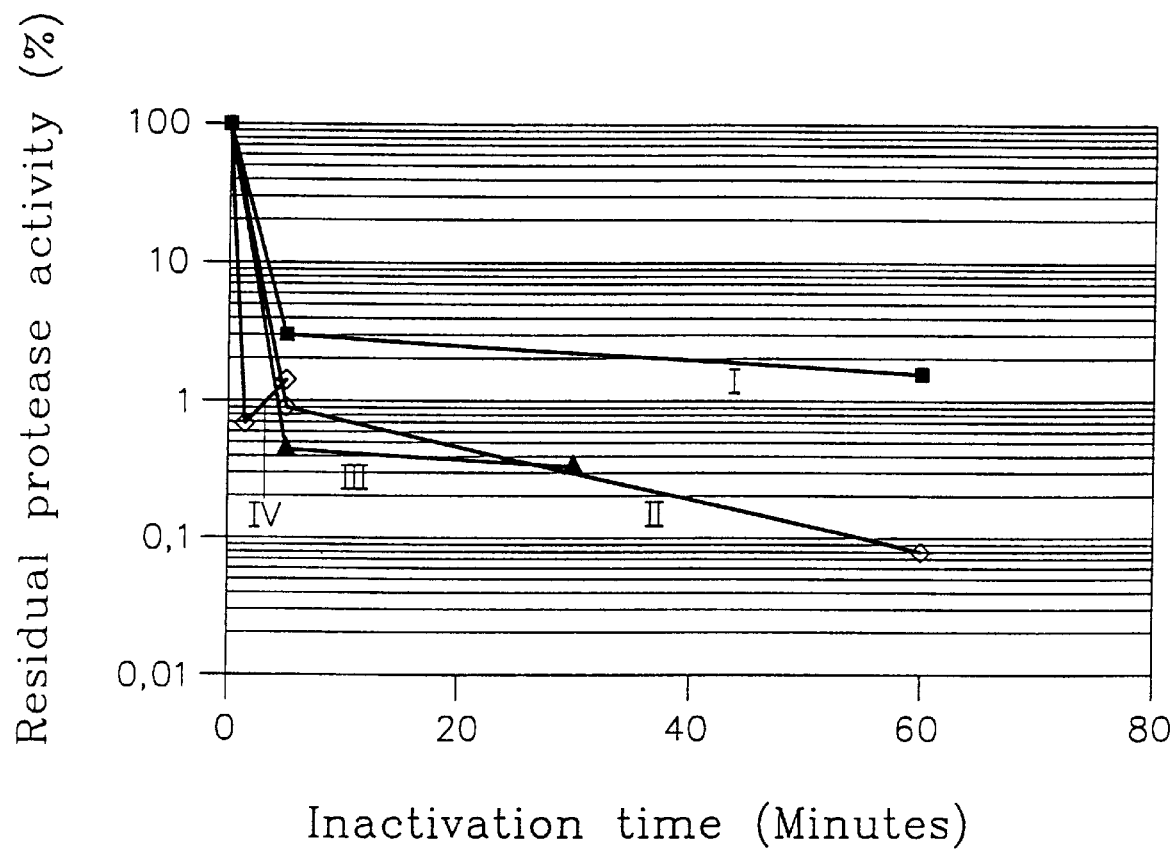
FIG. 2 shows the protease activity versus inactivation time at pH 3.5 and at 45° C. (I), at 50° C. (II), at 55° C. (III) and at 70° C. (IV), the experiments performed as described in Example 1.

The yield of the desired lipase activity is shown in FIG. 1, and the inactivation efficiency of undesired protease acivity is shown in FIG. 2.

It is seen that a treatment at 45° C. for 60 minutes at pH=3.5 offers a residual yield of 92% of lipase activity (FIG. 1) and less than 2% undesired protease activity (FIG. 2).

Figure 3:
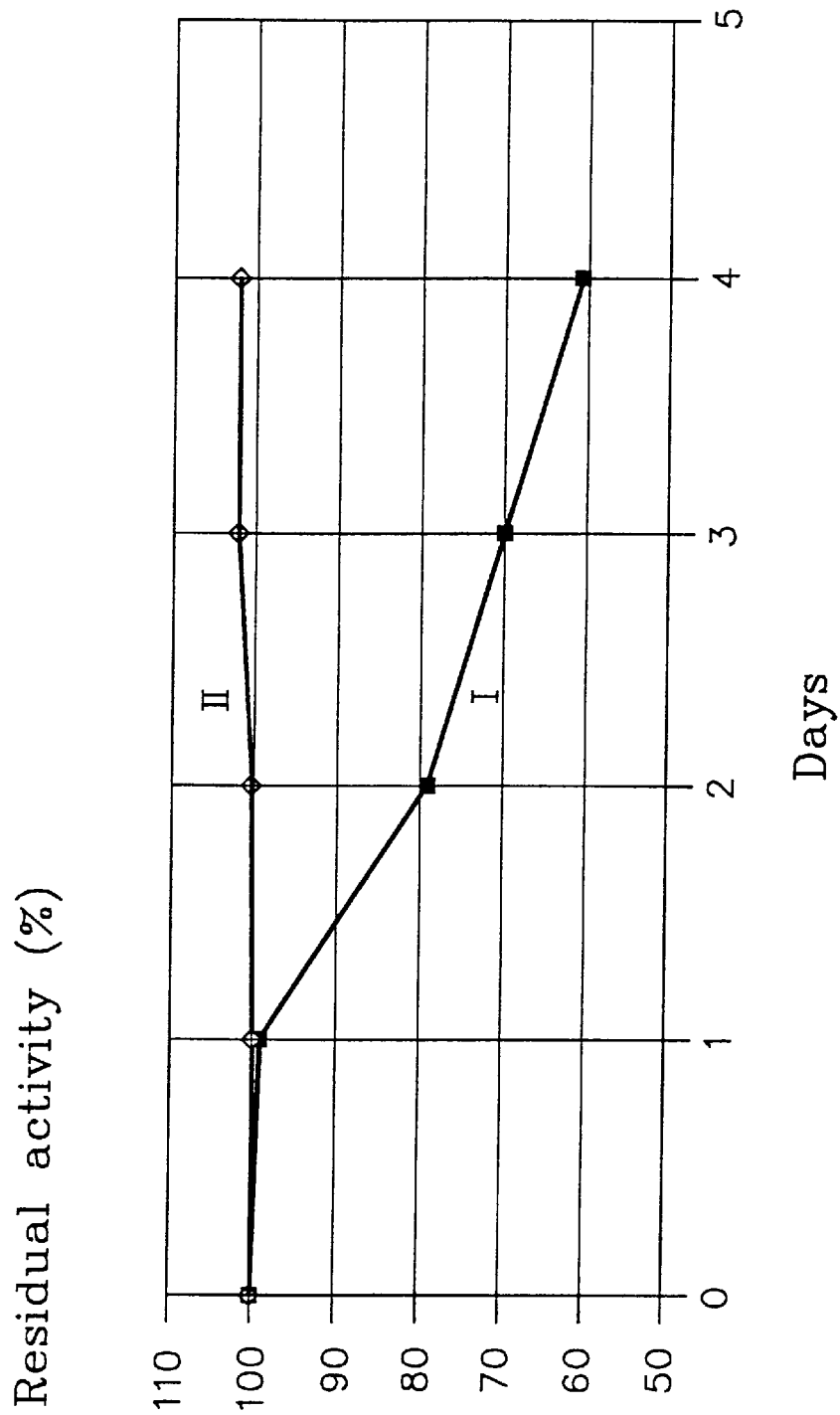
FIG. 3 shows a stability test with an untreated sample (I) and a sample subjected to pH 3.5 at 45° C. for 60 minutes (II), the experiment conducted as described in Example 1.

A stability test at 20° C. of the remaining lipase activity was conducted on the sample subjected to pH=3.5 and 45° C. for 60 minutes. The stability of the treated (II) and a non-treated concentrate (I) from the same batch is shown in FIG. 3. The graph shows that the treated sample is 100% stable whereas the untreated sample is unstable and loses 40% of the initial activity after just 4 days of storage.

EXAMPLE 2

Inactivation of Protease

This example describes the inactivation of undesired proteases in a drum filtrate at low pH leaving a desired lipase (the culture broth the same as in Example 1). Due to the high degree of instability of the desired lipase the method of invention was carried out already at the drum filtrate instead of after a concentration as described in Example 1.

Initially, the culture broth was subjected to solid/liquid separation by drum filtration. The drum filtrate was adjusted to pH=3.5 using 10% phosphoric acid and then heated to various temperatures within the interval of 45° to 70° C., (at 45° C. (I), at 50° C. (II), at 55° C. (III), at 60° C. (IV) and at 70° C. (V)).

After various minutes within the interval of 0–60 minutes samples were adjusted to pH=8.0 using 13% sodium hydroxide, cooled and analyzed for lipase and protease activity.

Figure 4:
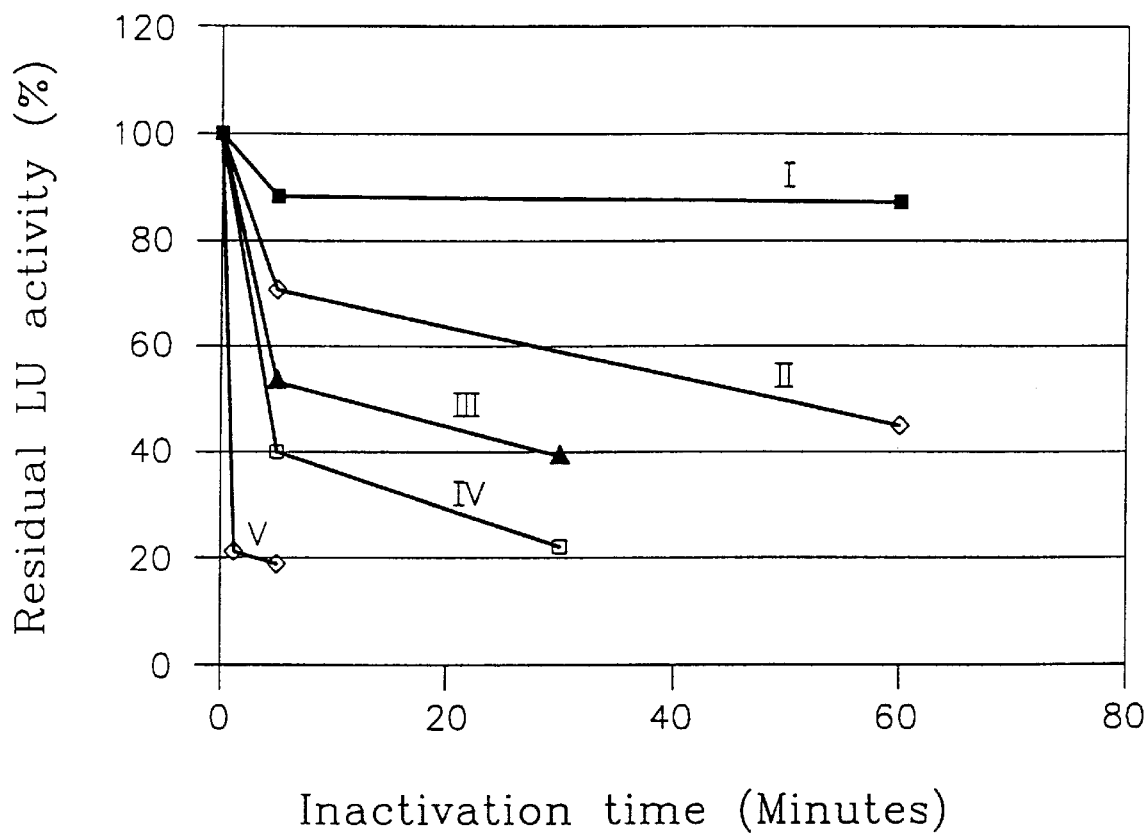
FIG. 4 shows the lipase activity versus inactivation time at pH 3.5 and at 45° C. (I), at 50° C. (II), at 55OC (III), at 60° C. (IV) and at 70° C. (V), the experiments performed as described in Example 2.
Figure 5:
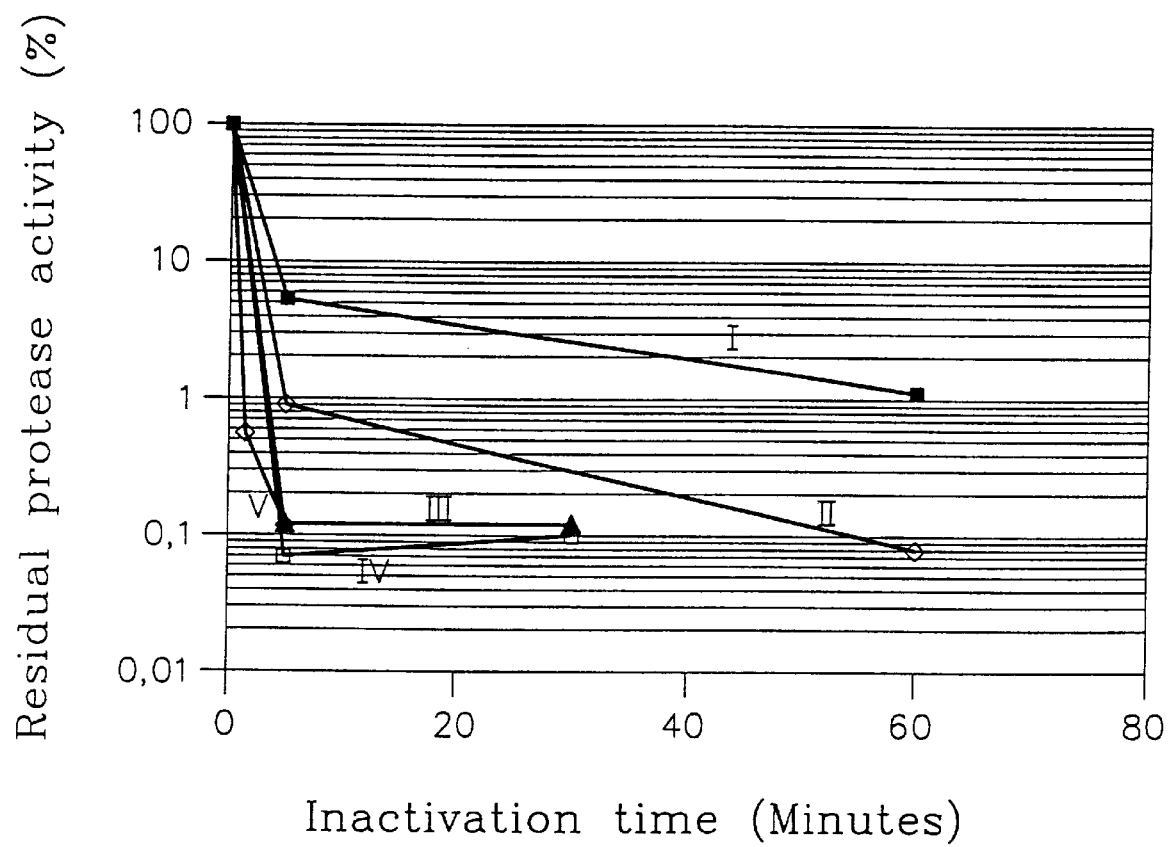
FIG. 5 shows the protease activity versus inactivation time at pH 3.5 and at 45° C. (I), at 50° C. (II), at 55° C. (III), at 60° C. (IV) and at 70° C. (V), the experiments performed as described in Example 2.

The yield of the desired lipase activity is shown in FIG. 4 and the inactivation efficiency of the undesired protease activity is shown in FIG. 5. It is seen that a treatment at 45° C. for 60 minutes at pH=3.5 offers a residual yield of 86% of lipase activity and less than 2% undesired protease activity.

EXAMPLE 3

Stability Tests

This example further describes the inactivation of undesired proteases in a drum filtrate at low pH leaving a desired lipase.

Initially, the culture broth (the culture broth the same as in Example 1) was subjected to solid/liquid separation by drum filtration. The drum filtrate was divided into three fractions. All three fractions were heated to 20° C. One fraction was adjusted to pH=2.5 using 20% phosphoric acid, the second fraction was adjusted to pH=10.7 using 13% sodium hydroxide and the third fraction, considered the untreated fraction, was adjusted to pH=5.5.

After 60 minutes the low pH and the high pH fractions were adjusted to pH=5.5 (using 13% sodium hydroxide to the fraction low pH fraction and 20% phosphoric acid to the high pH fraction). After pH adjustment the samples were cooled to 5° C. and all fractions were stored at said temperature for 14 days. In this way all fractions were kept at pH=5.5 and at 5° C. during storage. Samples from all three fractions were taken after 3, 7, 10 and 14 days and analyzed for lipase activity.

Figure 6:
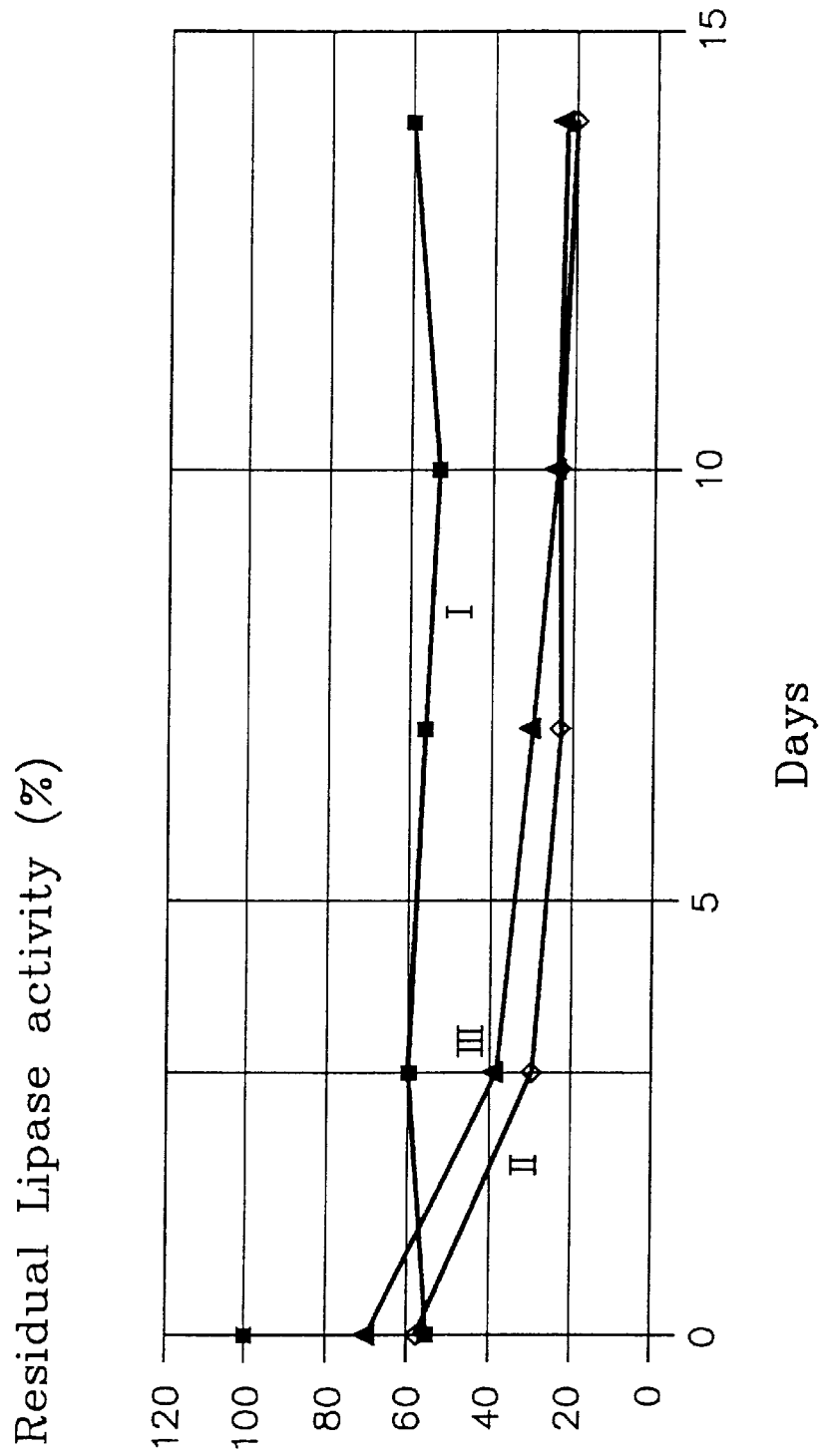
FIG. 6 shows stability tests with three different lipase samples: a sample treated at pH 2.5 at 20° C. for 60 minutes (I), a sample treated at pH 10.7 at 20° C. for 60 minutes (II) and an untreated sample (III), the experiments conducted as described in Example 3.

The stability during storage of the three fractions are shown in FIG. 6. It is seen that an acidic treatment at pH=2.5 for 60 minutes (I) is to be preferred over an alkaline treatment at pH=10.7 also for 60 minutes (II), both at 20° C., since the acidic treatment offers 100% stability whereas the alkaline treatment is highly unstable. The reference shows that the untreated sample (III) is also highly unstable.

The sample treated at pH=2.5 at 20° C. for 60 minutes is 100% stable after being treated using the method of the invention. Yield of the desired lipase was 60%.

EXAMPLE 4
Inactivation of Amylase

This example describes the inactivation of an undesired amylase in a drum filtrate at low pH leaving a desired cellulase.

A culture broth containing cellulase, obtained as described in WO 91/17243 by cloning *Humicola insolens* cellulase into an *Aspergillus oryzae* host, in which culture broth an undesired amylase is inactivated by use of the method of the invention.

The culture broth was subjected to solid/liquid separation by centrifugation. Subsequently the centrate was subjected to ultrafiltration using membranes with a cut off of 20 kD. The concentrate was heated rapidly to 70° C. and adjusted to pH=3.5 using 20% phosphoric acid and kept at said temperature and pH for 1 minute. After said holding time pH was readjusted to pH=7.0 with 13% sodium hydroxide and cooled rapidly to 40° C.

In this way the undesired amylase was inactivated leaving the desired cellulase intact as seen in Table 1 below. The undesired amylase is inactivated 100% leaving 96% of the desired cellulase activity intact.

TABLE 1

Inactivation of an undesired amylase from a lipase/amylase mixture at low pH and high temperature leaving the desired lipase.

|  | Desired Cellulase Yield | Undesired Amylase Yield |
| --- | --- | --- |
| Concentrate treated at pH = 3.5 for 1 min at 70° C. | 96% | 0% |

EXAMPLE 5
Inactivation of Amylase

This example describes the inactivation of an undesired amylase in a culture broth at high pH leaving a desired lipase.

A culture broth containing lipase, obtained as described in EP 305 216 by cloning *Humicola lanuginosa* lipase into an *Aspergillus oryzae* host, in which culture broth an undesired amylase is inactivated by use of the method of the invention.

Temperature was kept at 35° C. and pH was then adjusted to pH=10.7 using 13% sodium hydroxide and kept at said pH for 30 minutes whereby the amylase was inactivated. The culture broth was treated downstream using a solid/liquid separation by filtration to remove sludge leaving a clear filtrate.

Subsequently pH was adjusted to pH=8.0 using 13% sodium hydroxide and the liquid was cooled to 10° C.

By using this procedure the undesired amylase was inactivated selectively leaving the desired lipase as seen in Table 2 below. The undesired amylase is inactivated completely during the high pH treatment leaving the desired lipase.

TABLE 2

Inactivation of an undesired amylase from a lipase/amylase mixture at high pH and moderate temperature leaving the desired lipase.

|  | Desired Lipase Yield | Undesired Amylase Yield |
| --- | --- | --- |
| Culture broth treated at pH = 10.7 for 30 min at 35° C. | 93% | 0% |

EXAMPLE 6
Inactivation of Cellulase

This example describes the inactivation of undesired cellulases in a concentrate at low pH and at moderate temperature leaving the desired cellulase from *Humicola insolens*.

A culture broth containing *Humicola insolens* cellulase, obtained as described in U.S. Pat. No. 4,435,307 was subjected to the method of invention.

The desired cellulase with a pI=4.5 is responsible for approximately 25% of the total cellulase activity.

Initially, the culture broth was subjected to solid/liquid separation by drum filtration. Subsequently the drum filtrate was subjected to UF-concentration on membranes with a cut off of 20 kD.

The concentrate was adjusted to 20° C. Subsequently pH was adjusted to pH=2.0 using 20% phosphoric acid and kept at said pH for 60 minutes. After said holding time pH was adjusted to pH=8.0 using 13% sodium hydroxide.

As seen from Table 3 more than 95% of the undesired cellulase activity is inactivated leaving the desired cellulase activity intact.

TABLE 3

Inactivation of undesired cellulases from a mix of one desired and several undesired cellulases at low pH and at moderate temperature leaving the desired cellulase intact.

|  | Yield of desired cellulase | Yield of undesired cellulases |
| --- | --- | --- |
| pH = 2.0 at 20° C. for 60 min. | appr. 100% | <5% |

EXAMPLE 7
Inactivation of Protease

This example describes the inactivation of undesired proteases in a concentrate at low pH at low and at moderate temperature leaving the desired cellulase complex from *Humicola insolens*. As seen in Example 6 the complete cellulase complex is labile under acidic conditions. This Example therefore includes an example of the use of stabilizing components for the desired complete cellulase activity complex.

A culture broth containing *Humicola insolens* cellulase, obtained as described in U.S. Pat. No. 4,435,307 was subjected to the method of invention.

Initially, the culture broth was subjected to solid/liquid separation by drum filtration. Subsequently the drum filtrate was subjected to UF-concentration on membranes with a cut off of 20 kD.

The concentrate was divided into six equal fractions as shown in Table 4. All fractions but one was added CMC in the amount of 1% to investigate the stabilizing effects on the desired cellulase during inactivation of the undesired proteases.

In all cases 20% phosphoric acid was used to obtain the low pH values which were kept at said pH values for 60 minutes in all cases. After said holding time pH was in all cases adjusted to pH=8.0 using 13% sodium hydroxide.

As seen from Table 4 the effect of CMC at pH=3.0 is an increased cellulase yield during inactivation treatment. The effect of lowering the pH is a decreased cellulase yield but at the same time an increased efficiency of inactivation of the undesired proteases. The effect of increasing the temperature is a decreased cellulase yield.

TABLE 4

Inactivation of undesired proteases from a mix of cellulases/proteases at low pH and at low to moderate temperatures with and without CMC leaving the desired cellulase.

| Concentrate treated at | Desired cellulase Step yield | | Undesired proteases Step yield | |
|---|---|---|---|---|
| | With 1% CMC | Without CMC | With 1% CMC | Without CMC |
| ph = 2.5, 60 min, 3° C. | 57% | | 0% | |
| ph = 3.0, 60 min, 3° C. | 77% | 43% | <2% | <2% |
| ph = 3.5, 60 min, 3° C. | 90% | | <15% | |
| ph = 2.5, 60 min, 25° C. | 38% | | 0% | |
| ph = 3.5, 60 min, 25° C. | 95% | | <15% | |

EXAMPLE 8

Inactivation of Protease

This example describes the inactivation of undesired proteases in a concentrate at low pH leaving a desired catalase.

A culture broth containing *Scytalidium termophilum* catalase, obtained as described in WO 92/17571, was subjected to the method of invention.

The culture broth was subjected to flocculation as described in Table 5:

TABLE 5

Flocculaton of broth containing catalase.

| Added chemical Pr. Kg Culture broth | Amount (gram) |
|---|---|
| Water | 2000 |
| Na$_3$PO$_4$ | 20 |
| CaCl$_2$ × 2H$_2$O | 30 |
| pH | 8.0 |

TABLE 5-continued

Flocculaton of broth containing catalase.

| Added chemical Pr. Kg Culture broth | Amount (gram) |
|---|---|
| Anionic flocculant | 2 |

The flocculated broth was subsequently subjected to solid/liquid separation by drumfiltration.

The filtrate was divided into 2 fractions A & B. The two fractions were subjected to the treatment described in Table 6 below. pH was adjusted using 20% phosphoric acid.

TABLE 6

Treatments of two identical fractions containing both desired catalase and undesired protease.

| Treatments | Fraction A | Fraction B |
|---|---|---|
| Temperature | 40° C. | 40° C. |
| pH | 3.0 | 2.5 |

The fractions were treated for 0.5 and 1 hour; after said treatments the fractions were adjusted to pH=6.5 using 13% NaOH and cooled to 10° C.

Table 7 below illustrates both catalase and protease fields for the treated fractions.

Catalase activity was measured using a degradation of hydrogen peroxide. The time consumption, for a specified decrease in spectrophotometrically absorbance at a specified H$_2$O$_2$ concentration, is a measure of the catalase activity.

Protease activity was measured using ala-ala-pro-phe-p-nitro anilide SEQ ID NO:1 substrate described previously.

TABLE 7

Yields of desired catalase and undesired protease activities.

| | Fraction A | Fraction B |
|---|---|---|
| Treatment for 0.5 hour. | | |
| Yield of desired catalase activity | 69% | 62% |
| Yield of undesired protease activity | 14% | <1% |
| Treatment for 1 hour. | | |
| Yield of desired catalase activity | 61% | 58% |
| Yield of undesired protease activity | 11% | <1% |

It is seen that treatment of fraction B using a temperature of 40° C. for just 30 minutes at pH=2.5 offers a residual yield of 62% of catalase activity and less than 1% of undesired protease activity. Treatment of fraction A does not offer the same protease inactivation.

We claim:

1. A method for selective inactivation of an Aspergillus protease in a mixture of enzymes containing at least one a desirable non-Aspergillus enzyme and an acid labile protease, wherein the non-Aspergillus enzymes are recombinantly produced in an Aspergillus host that expresses said acid-labile protease, said method comprising the step of holding the mixture at a temperature of from 2° C. to 75° C. at a pH below 4.5 for at least 20 seconds.

2. A method according to claim 1, wherein said at least one desirable enzyme is selected from the group consisting of lipases, amylases, cellulases, oxidoreductases, xylanases, isomerases, proteases and peptidases.

3. A method according to claim 1, wherein the mixture of enzymes is contained in a culture broth.

4. A method according to claim 3, wherein the mixture of enzymes is contained in a clarified and concentrated culture broth.

5. A method according to claim 1, wherein said mixture of enzymes is adjusted to a pH below 4.0.

6. A method according to claim 1, wherein said temperature is in the range of from 10–70° C.

7. A method according to claim 1, wherein, after said inactivation, the level of the Aspergillus protease is less than 15% of its initial level.

8. A method according to claim 1, wherein, after said inactivation, the level of the desirable enzyme is more than 50% of its initial level.

9. A method according to claim 1, wherein, after said inactivation, the level of the Aspergillus protease is less than 15% of its initial level and the level of the desirable enzyme is more than 50% of its initial level.

10. A method according to claim 1, wherein two or more enzymes are desirable.

11. A method according to claim 1, further comprising, prior to said holding step, adding to said mixture at least one stabilizer of said desirable enzyme.

12. A method according to claim 1, further comprising, prior to said holding step, adding to said mixture at least one destabilizer of said Aspergillus protease.

13. A method according to claim 1, further comprising, prior to said holding step, adding to said mixture at least one stabilizer of said at least one desirable enzyme and at least one destabilizer of said Aspergillus protease.

* * * * *